(12) United States Patent
Yarger (10) Patent No.: US 7,794,421 B2
(45) Date of Patent: *Sep. 14, 2010

(54) ASPIRATOR SLEEVE AND TIP (75) Inventor: Richard J Yarger, Yakima, WA (US)

(73) Assignee: Surgimark, Inc., Yakima, WA (US)

( * ) Notice: Subject to any disclaimer, the term of this patent is extended or adjusted under 35 U.S.C. 154(b) by 776 days.

This patent is subject to a terminal disclaimer.

(21) Appl. No.: 11/303,702

(22) Filed: Dec. 15, 2005

(65) Prior Publication Data

US 2006/0095007 A1 May 4, 2006

Related U.S. Application Data

(63) Continuation of application No. 10/969,276, filed on Oct. 19, 2004, now Pat. No. 7,066,903, which is a continuation of application No. 10/153,420, filed on May 22, 2002, now abandoned.

(51) Int. Cl.
*A61M 1/00* (2006.01)
*A61M 25/00* (2006.01)

(52) U.S. Cl. .......................... 604/35; 604/118; 604/268

(58) Field of Classification Search ................ 604/6.16, 604/19, 35, 43–45, 48, 129, 242–243, 263–264, 604/513, 533, 540–542, 266; 433/91
See application file for complete search history.

(56) References Cited

U.S. PATENT DOCUMENTS

| 1,388,312 | A |   | 8/1921  | Seeger   |         |
|-----------|---|---|---------|----------|---------|
| 2,220,493 | A |   | 11/1940 | Pixler   |         |
| 3,308,825 | A | * | 3/1967  | Cruse    | 604/267 |
| 3,416,532 | A |   | 12/1968 | Grossman |         |
| 3,528,427 | A |   | 9/1970  | Sheridan |         |
| 3,965,901 | A |   | 6/1976  | Penny    |         |
| 4,398,910 | A |   | 8/1983  | Blake    |         |

(Continued)

FOREIGN PATENT DOCUMENTS

EP 0457220 A1 11/1991

(Continued)

OTHER PUBLICATIONS

Office Action dated Sep. 22, 2009, from U.S. Appl. No. 11/736,396, filed Apr. 17, 2007.

(Continued)

*Primary Examiner*—Kevin C Sirmons
*Assistant Examiner*—Andrew M Gilbert
(74) *Attorney, Agent, or Firm*—Christensen O'Connor Johnson Kindness PLLC (57) ABSTRACT

The present invention provides a coupling device for attaching a sleeve (40) to a surgical aspirator tip (10) that allows airflow between the external environment and the interior of the sleeve (40). The coupling device includes a male member (26) attached to the tip (10) and a female member (42) formed in the proximal end of the sleeve (40). The male member (26) includes at least one longitudinal groove (100). When the male member (26) is received into the female member (42), at least one venting channel (80) is defined between at least one longitudinal groove of the male member (26) and the inner surface of the female member (42). Venting channel (80) permits airflow between the external environment and the interior of the sleeve (40).

25 Claims, 6 Drawing Sheets

U.S. PATENT DOCUMENTS

| | | | |
|---|---|---|---|
| 4,451,257 A | | 5/1984 | Atchley |
| 4,465,481 A | * | 8/1984 | Blake .......................... 604/541 |
| 4,490,138 A | | 12/1984 | Lipsky |
| 4,648,871 A | | 3/1987 | Jacob |
| 4,662,871 A | * | 5/1987 | Rafelson ..................... 604/119 |
| 4,767,404 A | | 8/1988 | Renton |
| 4,867,747 A | * | 9/1989 | Yarger ......................... 604/263 |
| 5,024,615 A | | 6/1991 | Büchel |
| 5,360,414 A | | 11/1994 | Yarger |
| 5,690,487 A | | 11/1997 | Whitehouse |
| 5,817,050 A | * | 10/1998 | Klein ........................... 604/35 |
| 5,890,516 A | | 4/1999 | Talamonti |
| 5,899,884 A | | 5/1999 | Cover |
| 5,921,999 A | | 7/1999 | Dileo |
| 7,066,903 B2 | * | 6/2006 | Yarger ......................... 604/35 |
| 2001/0002432 A1 | | 5/2001 | Bugge |

FOREIGN PATENT DOCUMENTS

| | | |
|---|---|---|
| EP | 1364665 A1 | 11/2003 |
| FR | 2170858 A | 9/1973 |
| GB | 1531416 A | 11/1978 |
| WO | 96/04950 A1 | 2/1996 |

OTHER PUBLICATIONS

Office Action dated Feb. 3, 2010, from U.S. Appl. No. 11/405,270, filed Apr. 17, 2006.

EPO Communication dated Sep. 22, 2003, issued in corresponding European Application No. 03445061.9, filed May 20, 2003.

EPO Communication dated Aug. 31, 2004, issued in corresponding European Application No. 03445061.9, filed May 20, 2003.

EPO Communication dated Sep. 28, 2005, issued in corresponding European Application No. 03445061.9, filed May 20, 2003.

* cited by examiner

ASPIRATOR SLEEVE AND TIP

CROSS-REFERENCES TO RELATED APPLICATIONS

This application is a continuation of U.S. application Ser. No. 10/969,276, filed Oct. 19, 2004, now U.S. Pat. No. 7,066,903, which is a continuation of U.S. application Ser. No. 10/153,420, filed May 22, 2002, now abandoned, the entire disclosures of which are incorporated by reference herein.

FIELD OF THE INVENTION

This invention relates generally to surgical aspirators and surgical aspirator tip and sleeve combinations and more particularly to surgical aspirator tip and sleeve combinations that allow air to flow into the interior of the sleeve that is independent of the inflow of gases, fluids, and materials through the small holes in the sleeve.

BACKGROUND OF THE INVENTION

Surgical aspirators are used to remove fluids from the body of the patient. A surgical aspirator typically includes a tip that is inserted into a surgical site, wound, or other bodily orifice. The tip is generally elongated in shape and may include a handle or grip section to facilitate using the aspirator. The proximal end of the tip is connected to a tube that is connected to a suction pump that provides suction to the tip. The distal end of the aspirator tip is inserted into the patient and has one or more openings into which gases, fluids, and materials may flow.

Pieces of tissue and other debris may be suspended in the fluids and can clog the aspirator. Openings in the tip of the aspirator where the fluid first enters the device are particularly vulnerable to clogging. One solution to this problem involves covering the distal end of the aspirator tip with a sleeve formed with a plurality of small holes that prevent the tissue from reaching the opening of the aspirator tip while allowing the fluid sleeve become clogged, suction is no longer distributed uniformly among the remaining unclogged holes. This condition may cause too much suction in a particular area that may pull surrounding tissue into the holes of the sleeve causing injury to the patient.

One solution to this problem involves including additional orifices in the tip near the connection between the sleeve and tip. Because these additional orifices are spaced from the wound, bodily orifice, or surgical site the additional orifices are less likely to become clogged with tissue or debris. However, these orifices are vulnerable to being obstructed by the hands or fingers of the user of the aspirator. These orifices may also be obstructed or blocked by resting the aspirator tip and sleeve combination against another object such as the patient's body, a table, or dressings surrounding the surgical site.

Therefore, a need exists for improved surgical aspirator tip and sleeve combinations that allow air flow into the interior of the sleeve that is independent of the inflow of gases, fluids, and materials through the small holes in the sleeve.

SUMMARY OF THE INVENTION

The present invention provides a coupling device for attaching a sleeve to a surgical aspirator tip that allows airflow between the external environment and the interior of the sleeve. The coupling device includes a male member attached to the tip and a female member formed in the proximal end of the sleeve. The male member includes at least one longitudinal groove. When the male member is received into the female member, at least one venting channel is defined between at least one longitudinal groove of the male member and the inner surface of the female member. The venting channel provides communication between the interior of the sleeve and the external environment and permits airflow between the external environment and the interior of the sleeve.

In another aspect of the invention, the aspirator tip may include a handle that abuts the sleeve. At least one groove of the male member may be extended onto the handle so that air from the external environment may flow through the grooves and into at least one venting channel.

As a further aspect, the female member may include at least one cross-hole in communication with both the interior of at least one venting channel and the external environment.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
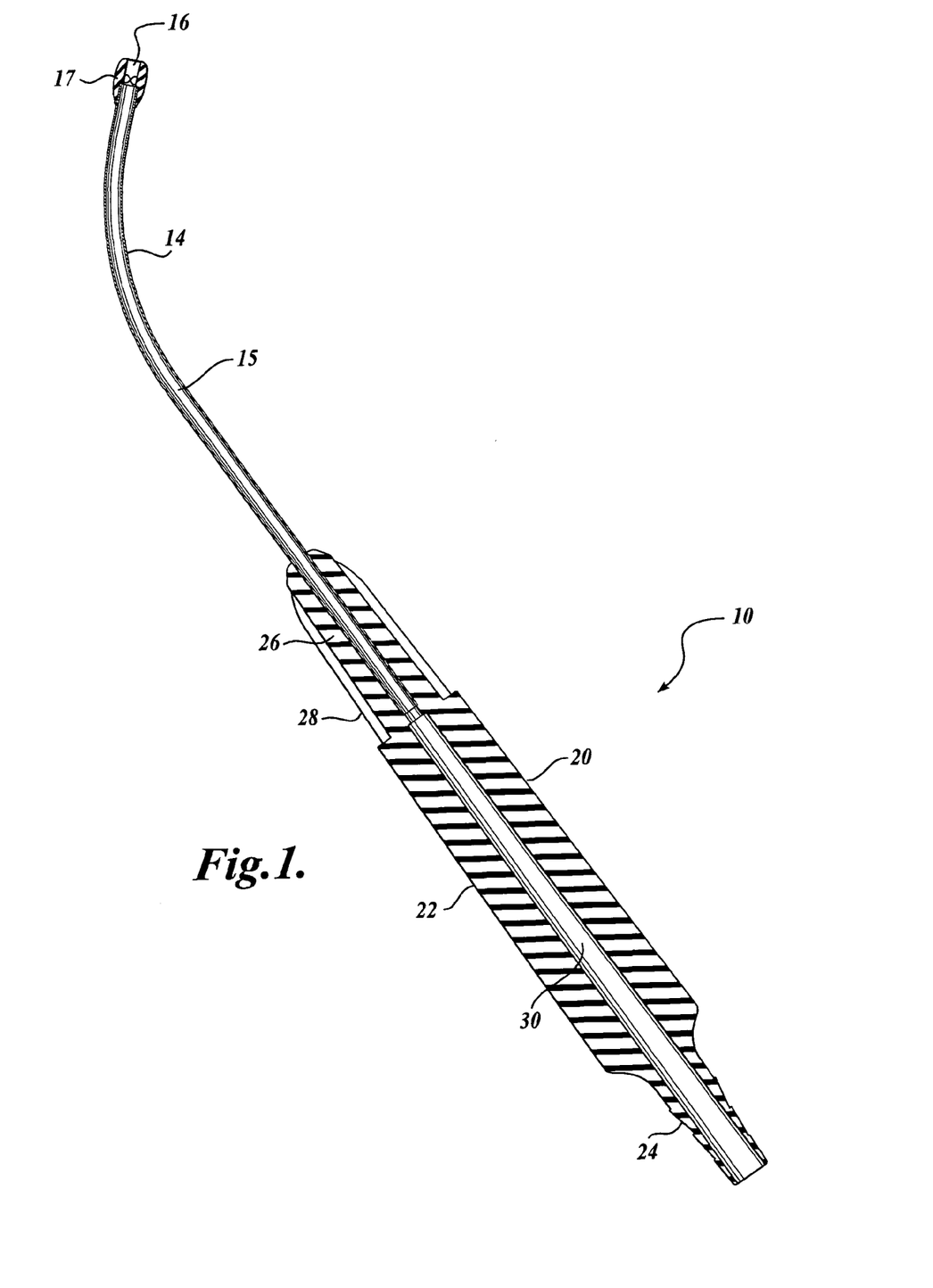
FIG. 1 is a cross-sectional view of an aspirator tip including a male coupling member of the coupling device constructed in accordance with the present invention.

FIG. 1 depicts the tip 10 of a surgical aspirator. The tip 10 generally includes a hollow tubular neck member 14 that may be inserted into the wound, bodily orifice, or surgical site and an elongated handle member 20. The handle member 20 defines a longitudinal internal channel 30. The handle member 20 may include a grip section or member 22 for gripping the tip 10, a tube coupling member 24 that is used to attach the tip 10 to a tube 38 (depicted in FIG. 5) that in turn is connect to a source of suction (not shown), and a male coupling member 26 for attaching a sleeve 40 (see FIGS. 4-6) to the tip 10. The handle member 20 may be constructed from a rigid or semi-rigid, resiliently deformable material that is adaptable for use in the medical arts. Preferably, polymeric or resinous plastic is used. The tubular neck member 14 may be constructed from metals such as steel or from the same or similar materials used to construct the handle member 20.

The proximal end of the tubular neck member 14 is attached to the distal end of the handle member 20 so that the interior 15 of the tubular neck member 14 is in communication with the internal channel 30 in the handle member 20. The distal end of the neck portion 14 includes at least one opening or orifice 16 into which gases, fluids, and materials can flow. A tip guard 17 open at its distal end may be attached to the distal end of the tubular neck member 14. Tip guard 17 may include additional orifices located circumferentially about tip guard 17. In this manner, gases, fluids, and materials may flow through these additional orifices and into the opening 16 in the distal end of the neck portion 14. Gas, fluid and material flow down the neck 14 and into the handle member 20 of the tip 10. A suction tube 38 may be attached to the tube coupling member 24 of the tip 10. The free end of the suction tube 38 may then be attached to a source of suction (not shown), such as a suction pump, to provide suction to the aspirator. In this manner, suction supplied to the tube 38 flows through the handle member 20, into the neck member 14, and out opening 16.

Figure 2:
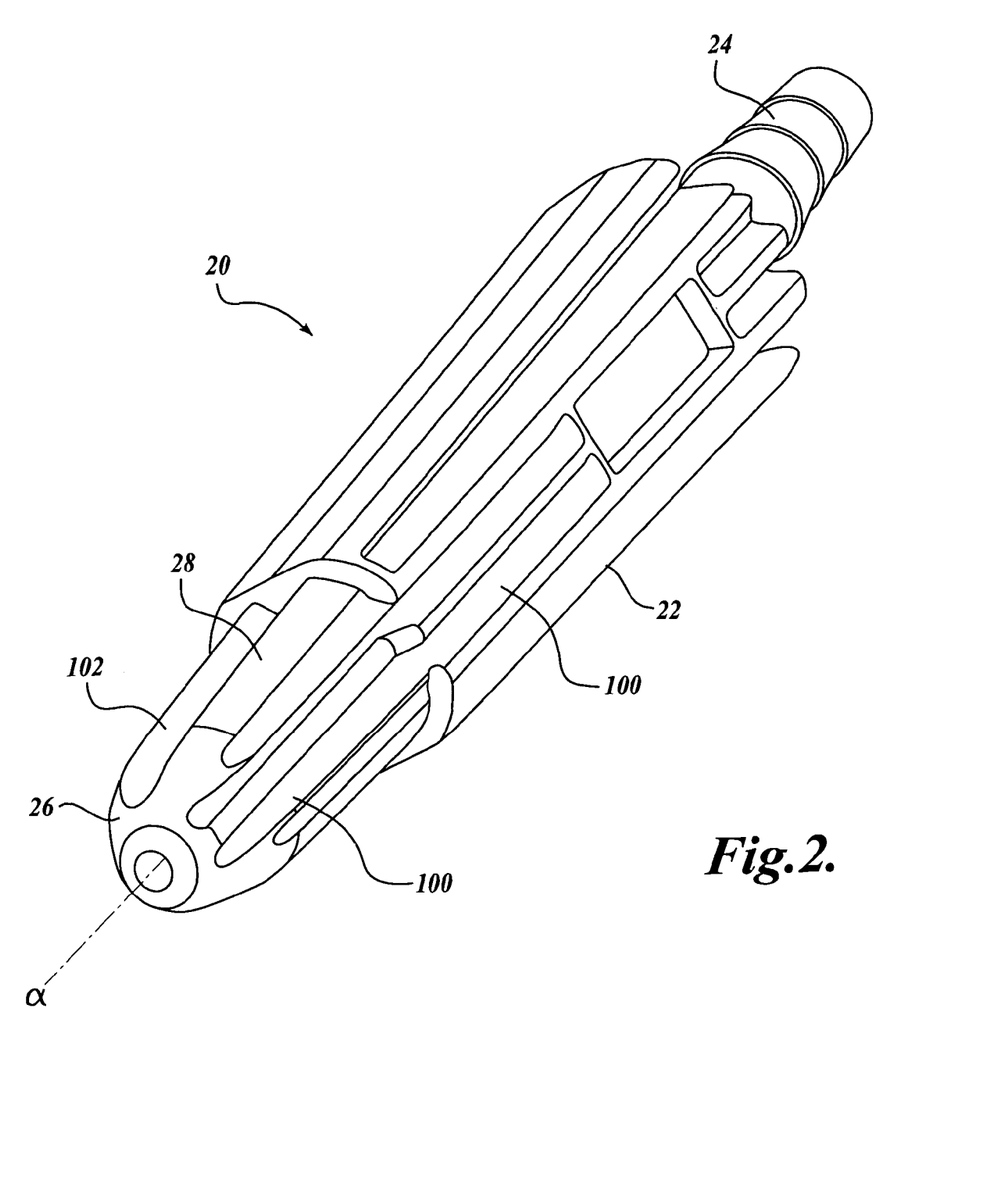
FIG. 2 is an isometric view of the distal end of an aspirator tip from a point located to the side of the distal end of the aspirator tip wherein the neck has been omitted to better illustrate the male coupling member of a coupling device constructed in accordance with the present invention.

Referring to FIG. 2, the male coupling member 26 includes an outside surface 28. The male coupling member 26 may be formed in the distal portion of the handle member 20 or attached to the handle member 20 as a separate component. Alternatively, the male coupling member 26 may be attached to the neck member 14 and not attached to the handle member 20. The male coupling member 26 may be between about [40 and 55 mm] long in the longitudinal a direction.

In one embodiment, the male coupling member 26 is generally tapered along its longitudinal axis a so that the cross-sectional area of the proximal end is greater than the cross sectional area of the distal end. In alternate embodiments, other profiles where the cross-sectional areas of the proximal and distal ends are approximately equal. Along its lateral axis, the proximal end of the male coupling member 26 may be between about [4 and 20 mm] and the distal end may be between about [4 and 20 mm]. In one embodiment, the proximal cross-sectional area of the male coupling member 26 is less than the cross-sectional area of the distal end of the grip member 22.

The cross-sectional shape of the male coupling member 26 may remain constant or vary (as depicted in FIG. 2) along the longitudinal axis $\alpha$. The male coupling member 26, excluding grooves 100, may have any cross-sectional shape, but preferably has a cross-sectional shape that is generally round, ovoid, square, rectangular, triangular, hexagonal, or other closed shape. To aid in attaching or removing the sleeve 40, the male coupling member 26 may also include ridges or grooves such as longitudinal grooves 102 (depicted in FIG. 2) spaced from grooves 100 along the circumference of male coupling member 26.

Handle member 20 may include at least one groove 100 extending longitudinally along the outside surface of handle member 20. In one embodiment, grooves 100 extend from the distal to the proximal end of male coupling member 26. Furthermore, grooves 100 may extend onto a section of the grip member 22 from its distal end. Alternatively, separate grooves may be included in the grip member 22 that are in communication or intersect with grooves 100. Grooves 100 may be between 1 and 7 mm deep and 1 and 10 mm wide. Grooves 100 may have any cross-sectional shape such as U-shaped, V-shaped or other suitable groove shape.

Returning to FIG. 1, tube coupling member 24 may include a tiered section that is coupled to the tube 38 (see FIG. 5) by inserting one or more of the tiers having a smaller cross-sectional area into the tube 38, however, any tube coupling mechanism may be used. The tube 38 may be constructed from any tubular material suitable for transmitting suction forces to a surgical aspirator and gases, fluids and materials from a surgical site known in the medical arts.

The grip member 22 is a generally elongated member and may include grooves, ridges, other projections, or depressions that may aid the user in gripping the tip 10. The grip member 22 is suitably sized to be received into an average sized hand but larger or smaller grip sections may be constructed for larger or smaller hands respectively. Generally, the grip member 22 may be between about [35 and 80 mm] long and have a cross-sectional width between about [12 and 30 mm] and a cross-sectional height between about [12 and 30 mm]. The grip member 22 may also be tapered or include contours along its longitudinal axis for a more comfortable grip.

Figure 3:
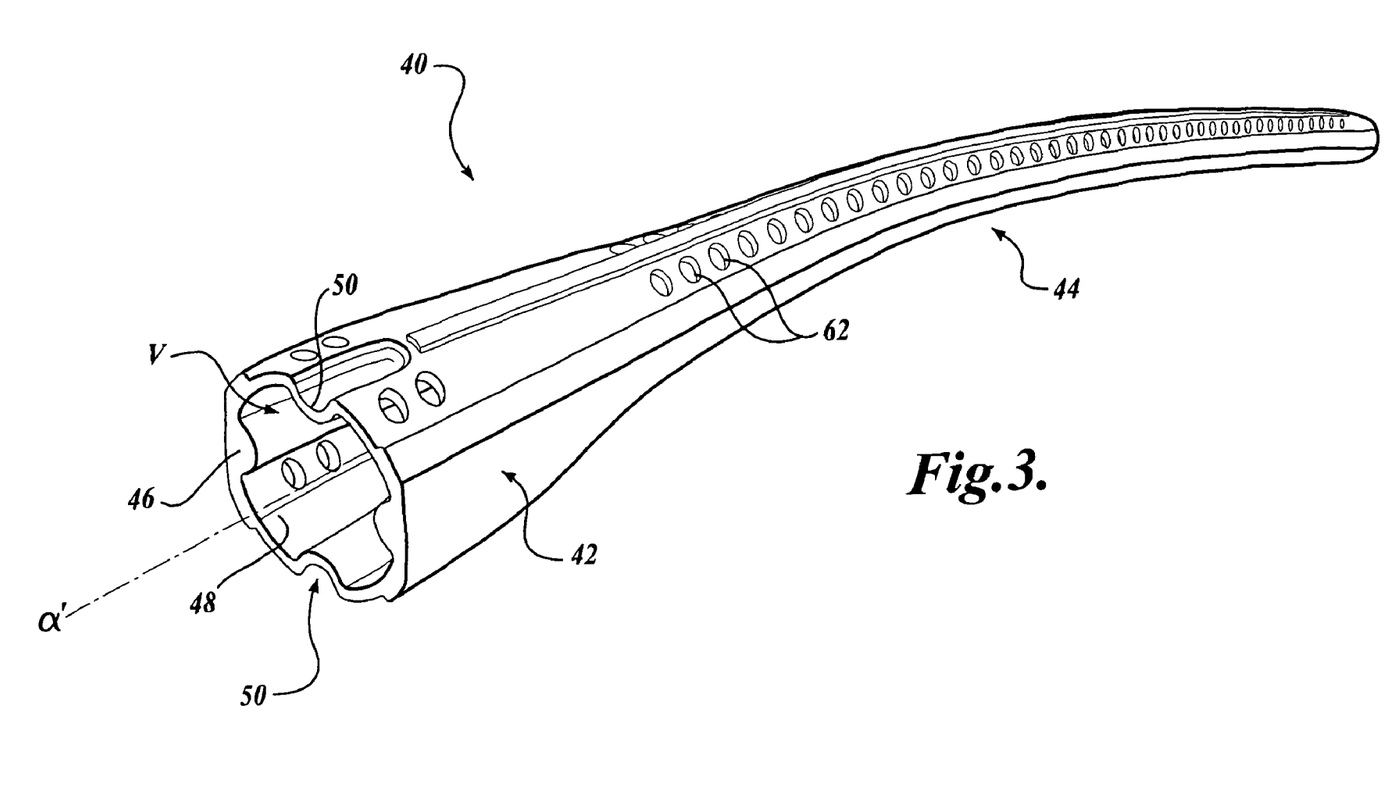
FIG. 3 is an isometric view of the proximal end of a sleeve from a point located to the side of the proximal end of the sleeve including a female coupling member of a coupling device constructed in accordance with the present invention.

Referring to FIG. 3, the sleeve 40 includes a female coupling member 42 and a tapered distal section 44. The female coupling member 42 can be formed in the sleeve 40 or attached to it as a separate component. The female coupling member 42 includes a wall 46 with an inside surface 48 that defines an internal receiving volume V. The wall 46 also includes inwardly extending longitudinal projections 50. In one embodiment, the inwardly extending projections 50 traverse a longitudinal section of the female coupling member 42. Preferably, the projections 50 longitudinally traverse a section of the female coupling member 42 that starts at its proximal end and terminates a predetermined distance from the proximal end. Alternatively, the projections 50 may traverse the entire longitudinal length of the female coupling member 42.

Referring to the embodiment of the present invention depicted in FIG. 3, the female coupling member 42 is generally tapered along its longitudinal axis $\alpha'$ so that the cross-sectional area of the proximal end is greater than the cross-sectional area of the distal end. In alternate embodiments, other profiles may be used such that the cross-sectional areas of proximal and distal ends are approximately equal. In yet another embodiment, the female coupling member 42 is tapered or contoured to approximate the taper or contour of the male coupling member 26. Along its lateral axis, the proximal end of the female coupling member 42 may be between about [8 and 24 mm] and the distal end may be between about [8 and 24 mm].

The cross-sectional shape of the female coupling member 42 may remain constant or vary (as depicted in FIG. 3) along the longitudinal axis $\alpha'$. The female coupling member 42 may have any cross-sectional shape but is preferably generally round, ovoid, square, rectangular, triangular, hexagonal, or other closed shape. In an alternate embodiment, the cross-sectional shape of the female coupling member 42, excluding the projections 50, approximates the cross-sectional shape of the male coupling member 26. The female coupling member 42 may also include grooves or ridges along its external surface as desired to aid in attaching or removing the sleeve 40.

The tapered section 44 of the sleeve 40 is generally hollow and includes a plurality of spaced orifices 62 that allow gases, fluids, and materials to flow into the interior of the sleeve 40. The orifices 62 are preferably round or ovoid but other shapes may be used. The orifices 62 are sized to permit the inflow of gases, fluids, and materials of a size that will not clog the opening 16 in the neck member 14 into the interior of the sleeve 40. However, larger materials, such as body tissue, are unable to pass through the orifices 62 and may clog them.

The tapered section 44 may be contoured to match the contours present in the neck member 14. The tapered section 44 may also be constructed from a material suitably flexible to conform to the shape of an aspirator neck 14 member inserted therein. Suitable materials to construct the tapered neck include rigid or semi-rigid, resiliently deformable materials adaptable for use in the medical arts such as polymeric or resinous plastic. The tapered section 44 may also include ribs, ridges, and other projections as well as grooves and depressions to lend structural support and aid in conducting gases, fluids, and materials into the interior of the sleeve 40.

Figure 4:
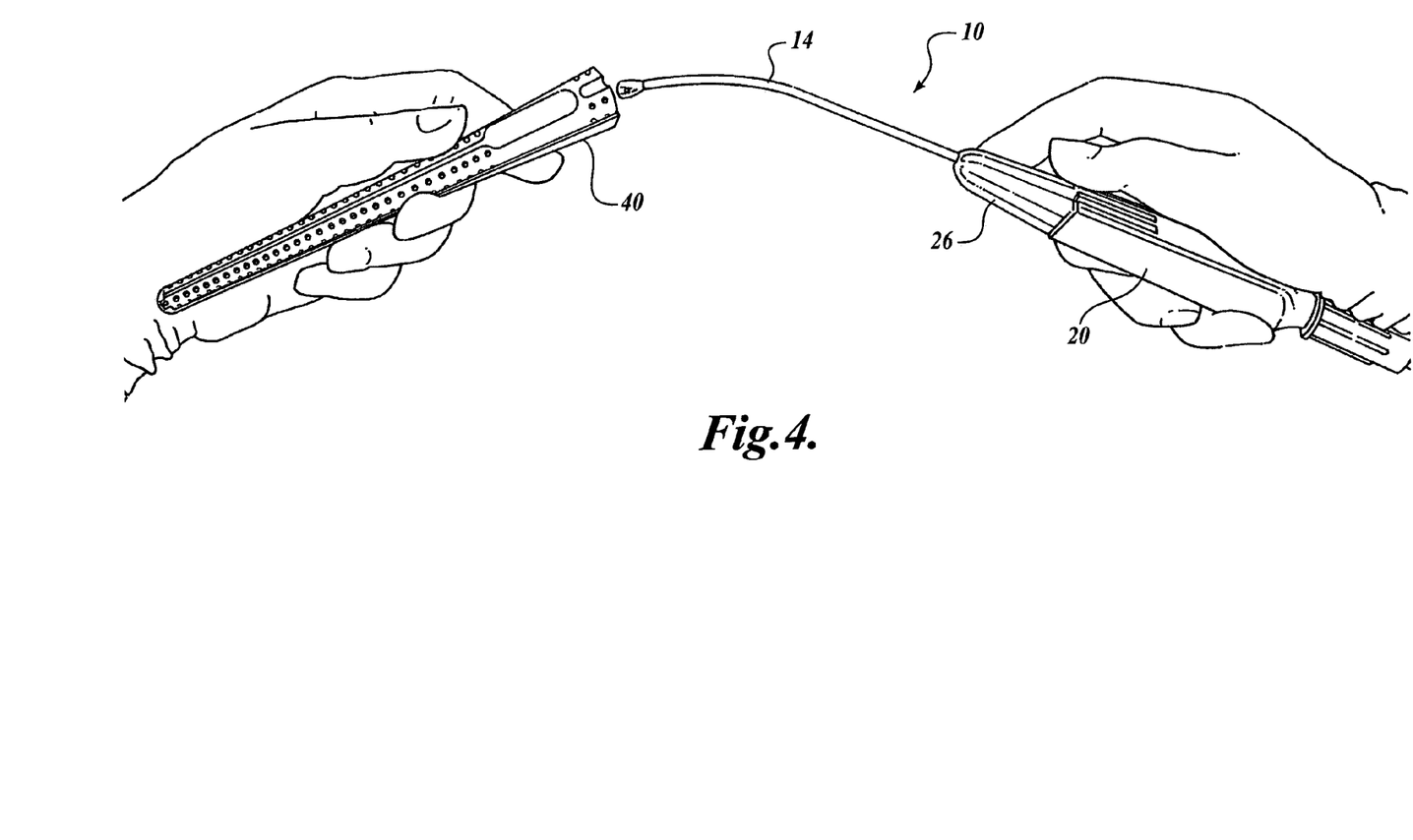
FIG. 4 is an isometric view of the aspirator tip of FIG. 1 being received into the sleeve of FIG. 3.
Figure 5:
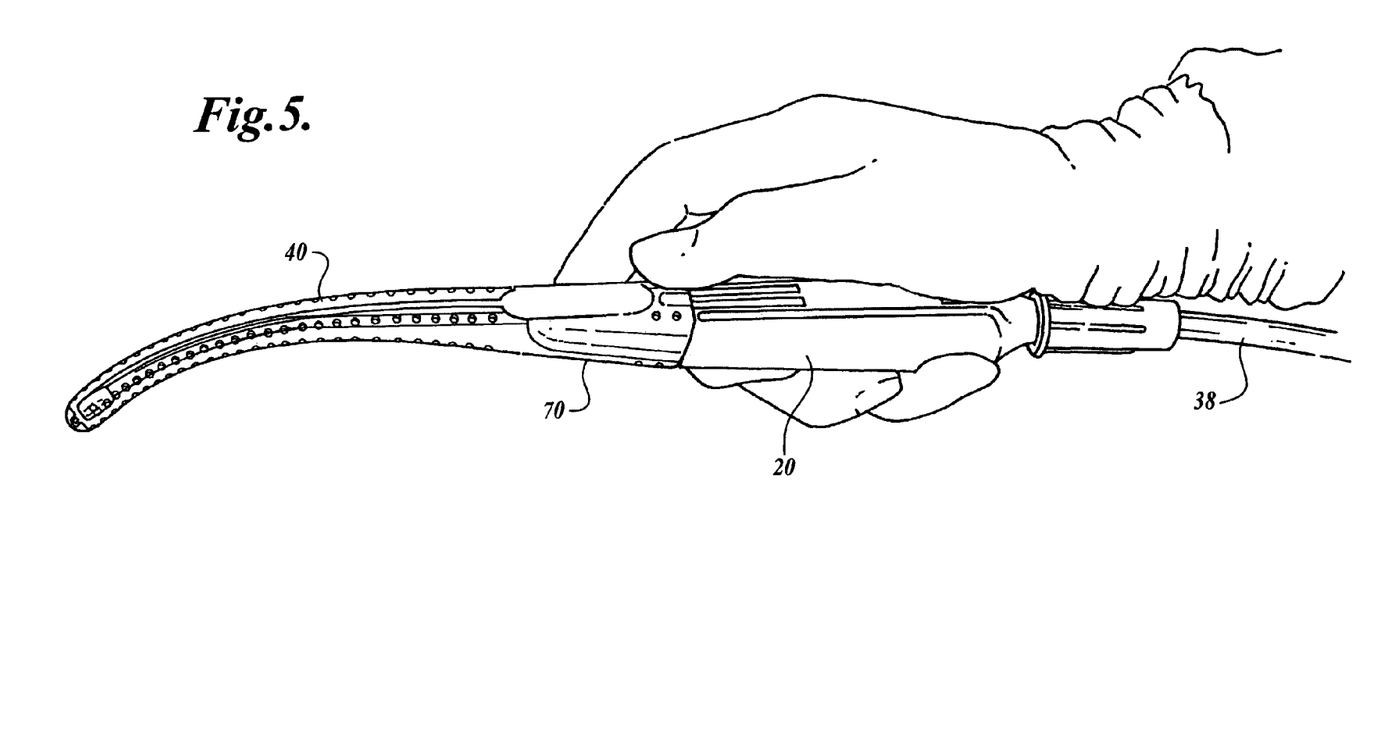
FIG. 5 is an isometric view of the sleeve of FIG. 3 coupled to the aspirator tip of FIG. 1.
Figure 6:
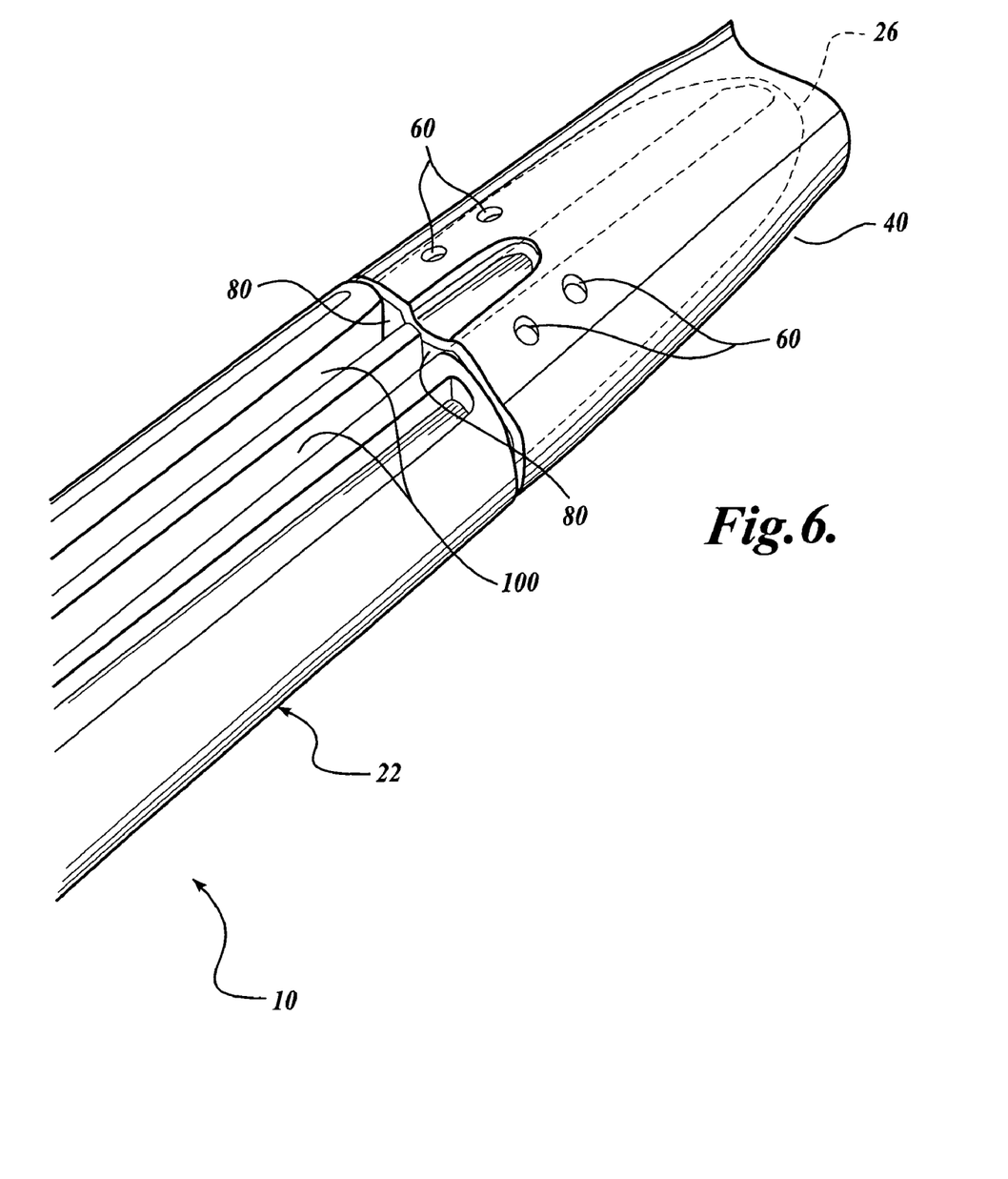
FIG. 6 is an isometric view of a coupling device constructed in accordance with the present invention from a point located proximally and spaced from the coupling device.

Referring now to FIGS. 4 and 5, the sleeve 40 slides over the neck 14 of the tip 10 so that the neck 14 of the tip 10 may be completely encased by the sleeve 40. Generally, the sleeve 40 is attached to the tip 10 at the handle member 20 by a coupling device. The coupling device includes a tip coupling member such as the male coupling member 26 and a sleeve coupling member such as the female coupling member 42. The male coupling member may be received into the receiving volume V see (FIG. 3) of the female coupling member 42. A coupled region 70 is formed where the male coupling member 26 is inserted into the female coupling member 42. The inside surface 48 of the wall 46 of the female coupling member 42 contacts the outside surface 28 of the male coupling member 26. Portions of the inside surface 48 of the female coupling member 42 do not contact the outside surface 28 of the male coupling member 26. Particularly, the sections of the inside surface 48 of the female coupling member 42 adjacent to grooves 100 may not contact the outside surface 28 of male coupling member 26. Consequently, venting channels 80 are formed between the inside surface 48 of the wall 46, the outside surface 28 of the male coupling member 26 as depicted in FIG. 6. These venting channels 80 allow air to flow between the external environment into the interior of the sleeve 40.

Along the coupling region 70, the cross-sectional area of the male coupling member 26 is less than the corresponding cross-sectional area of the female coupling member 42 directly adjacent. In this manner, referencing to FIG. 6, the outside surface 28 of the male coupling member 26 is not in constant continuous contact with the inside surface 48 of the wall 46 of the female coupling member 42. In the areas where the inside surface of the female coupling member 42 is not in contact with the outside surface 28 of the male coupling member 26, gaps or venting channels 80 are formed. Each individual venting channel may be in communication with other venting channels, the external environment, and/or the interior of the sleeve 40 as required to provide communication between the external environment and the interior of the sleeve 40.

With the sleeve 40 in place, the distal end of the tip 10 and sleeve 40 combination may be inserted into the wound, surgical site, or bodily orifice to remove fluids therein. Suction flows from the suction source (not shown) through the tube 38 and into the handle member 20. Suction traverses the handle member 20 and into the neck member 14. Suction travels up the neck and pulls gases, fluids, and small materials into the opening 16. The gases, fluids, and materials inside the sleeve 40 flow from the wound, surgical site, or bodily orifice into the sleeve 40 through the plurality of orifices 62 in the tapered section 44. When the orifices 62 become clogged such that the flow of gases, fluids, and materials into the interior of the sleeve 40 is restricted, air flow is available to the sleeve through the venting channels 80. Air provided by the venting channels may prevent uneven distribution of suction forces over any unclogged orifices 62. If the suction force is concentrated over too few orifices 62, the tissue surrounding the wound, surgical site, or orifice could be pulled into the orifices 62 in the sleeve 40 possibly causing discomfort, pain, and injury to the patient.

In one embodiment depicted in FIGS. 5 and 6, the distal end of the grip member 22 abuts the proximal end of the female coupling member 42. In yet another embodiment, the distal end of the grip member 22 abuts the proximal end of the female coupling member 42 and is of suitable size and shape to obstruct the venting channels 80. As mentioned above, longitudinal grooves 100, best seen in FIG. 6, may extend onto grip member 22 from the distal end. Air may flow through the portion of grooves 100 located in handle member 22 into the venting channels 80. This configuration may prevent both the hands of the user and the distal end of the grip member 22 from interfering with the air flow through the venting channels 80.

Cross-holes 60 may be formed in the portion of the wall 46 between the venting channels 80 and the external environment to provide another means by which air may enter the venting channels 80. Because the handle 18 is not generally in contact with the tissue or fluids at the surgical site, the portion of grooves 100 located in the handle member 22 and cross-holes 60 in the sleeve 40 are unlikely to become clogged with tissue. Therefore, a constant airflow is available inside the sleeve 40 and particularly in the area surrounding opening 16 in the tip 10. This airflow prevents uneven distribution of suction to the holes of the sleeve 40.

As a non-limiting example, the tip 10 of the present invention may be formed by injection molding. For illustrative purposes, one non-limiting example of a method by which the tip 10 may be constructed will be provided herein.

A removable tip guard core may be inserted into the distal end of the neck 14. The tip guard core and the neck 14 may then be placed in the tip guard mold. The tip guard mold includes an upper and a lower portion. Each portion of the tip guard mold contains a portion of a mold cavity. Further, the mold may include inwardly extending projections that extend into the mold cavity to form additional openings in the tip guard 17.

Both portions of the tip guard mold are coupled together to define the mold cavity therebetween. At least one inlet channel is included in the mold to allow the inflow of material into the mold cavity. An injection nozzle may inject material through the inlet channel and into the mold cavity. The injected material fills the mold cavity and surrounds a section of the tip guard core.

After the material injected into the mold cavity has cured, the mold portions are separated and the neck 14 and newly formed tip guard 17 are removed from the mold. Next, the tip guard core may be removed from the distal end of the tip guard.

The handle member 20 is formed similarly to the tip guard 17. A handle member core is inserted into the proximal end of the neck 14. The neck 14 and the handle member core are then placed inside handle member mold. The handle member mold includes a top portion and a lower portion each including a portion of the mold cavity. When both portions are coupled together, the mold cavity is defined therebetween. At least one inlet channel in communication with the mold cavity and the external environment is defined in the mold. An injection may then inject material through the inlet channel into the mold cavity. The injected material fills the mold cavity around a section of the neck 14 and the handle member core.

After the injected material has had an opportunity to cure, the handle member 20, neck 14, and the handle member core are removed from the mold. The handle member core is then removed from the proximal end of the handle member 20.

Both the tip guard core and the handle member core may be composed of core materials known in the art such as hardened tool steel or other suitable core material. Similarly, the molds may be constructed from materials known in the art such as hardened tool steel or other suitable mold material. The material injected may include polymeric or resinous plastics.

In the process described above, both the handle member 20 and tip guard 17 are formed around the neck 14. Therefore, no additional assembly is required. Further, a strong fluid tight bond is formed between the neck 14 and both the tip guard 17 and the handle member 20.

While one method of forming the tip is depicted in this application, it is apparent to one of ordinary skill in the art that alternate equivalent methods are available. For example, both the handle member 20 and the tip guard 17 could be molded within a single mold at the same time. Furthermore, the tip guard core could be inserted through the proximal end instead of the distal end.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. In a sleeve and surgical aspirator tip assembly, a junction defined between the sleeve and surgical aspirator tip assembly that allows airflow between the external environment and an interior of the sleeve; wherein the surgical aspirator tip assembly comprises a hollow neck section that has at least one opening in its distal end through which fluids and materials enter the aspirator tip assembly; and the junction comprises:
    (a) an elongate male coupling member extending from a proximal end of the hollow neck section and defining an internal channel in communication with an interior of the hollow neck section allowing gases, fluid, or materials to flow between the interior of the hollow neck section and the internal channel of the male coupling member, and wherein the male coupling member has a thickness extending between an exterior surface of the male coupling member and the internal channel of the male coupling member, wherein the male coupling member comprises at least one elongate groove extending longitudinally along an exterior portion of the male coupling member, the at least one elongate groove being of a depth less than the thickness of the male coupling member;
    (b) an elongated grip member extending from a proximal end of the male coupling member, the elongated grip member comprising at least one longitudinal groove extending along an exterior portion of the elongated grip member, wherein said at least one elongate groove of the male coupling member is in fluid flow communication with the at least one longitudinal groove of the elongated grip member;
    (c) a female coupling member formed in a proximal end of the sleeve;
    (d) wherein the male coupling member is received into the female coupling member to form a friction fit connection therebetween and secure the sleeve to the surgical aspirator tip assembly; and
    (e) at least one venting channel in communication with the interior of the sleeve and the external environment, said venting channel:
        (i) is defined by the at least one elongate groove of the male coupling member and an internal surface of the female coupling member; and
        (ii) allowing airflow between the external environment and the interior of the sleeve.

2. The junction between the sleeve and aspirator tip assembly of claim 1, wherein the elongated grip member defines an internal channel in communication with the internal channel in the male coupling member allowing gases, fluid, or materials to flow between the internal channel in the male coupling member and the internal channel of the elongated grip member.

3. The junction between the sleeve and aspirator tip assembly of claim 1, wherein at least one portion of the female coupling member defining a portion of the at least one venting channel comprises at least one cross-hole in communication with the interior of the venting channel and the external environment.

4. The junction of claim 2, wherein the elongated grip member has a thickness extending between the exterior portion of the grip member and the internal channel of the grip member, and wherein the at least one longitudinal groove extending along the exterior portion of the grip member is of a depth less than the thickness of the grip member.

5. The junction between the sleeve and surgical aspirator tip assembly of claim 1, wherein a distal end of the elongated grip member is positioned to abut a proximal end of the female coupling member when the male coupling member is received into the female coupling member to substantially prevent longitudinal movement of the sleeve along the surgical aspirator tip assembly in a first direction.

6. The junction between the sleeve and aspirator tip assembly of claim 1, wherein the elongated grip member is positioned exterior of the sleeve when the male coupling member is received into the female coupling member such that the elongated grip member is manually graspable by a user.

7. A sleeve and aspirator tip combination comprising:
    (a) an elongated aspirator tip comprising
        (i) a neck comprising an internal channel with at least one orifice located near a distal end of the neck into which gases, fluid, and material may flow;
        (ii) an elongate tip coupling section defining an internal channel;
        (iii) at least one longitudinal groove extending along at least a portion of an exterior of the tip coupling section; and
        (iv) wherein the neck is connected at its proximal end to a distal end of the tip coupling section and the internal channel of the tip coupling section is in communication with the internal channel in the neck allowing gases, fluid, and material flowing through the internal channel in the neck to flow into the internal channel in the tip coupling section; and
    (b) a tapered elongated sleeve comprising
        (i) a sleeve coupling section comprising a generally tubular wall that defines an internal receiving volume; and
        (ii) a plurality of orifices spaced from the sleeve coupling section arranged along the sleeve to provide communication between the external environment and an interior of the sleeve;
    (c) wherein the aspirator tip is coupled to the sleeve by inserting the tip coupling section into the receiving volume of the sleeve coupling section to form a coupled region; and
    (d) at least one venting channel is formed between a portion of the at least one longitudinal groove extending along the exterior of the tip coupling section and the tubular wall of the sleeve coupling section allowing communication between the external environment and the interior of the sleeve.

8. The sleeve and aspirator tip combination of claim 7, wherein the elongated aspirator tip comprises an elongated grip member located at a proximal end of the tip coupling section.

9. The sleeve and aspirator tip combination of claim 8, wherein an extension of the at least one longitudinal groove extending along an exterior portion of the elongated aspirator tip continues along an exterior portion of the elongated grip member.

10. The sleeve and aspirator tip combination of claim 7, wherein the tubular wall of the sleeve coupling section comprises at least one cross-hole in communication with the external environment and the at least one venting channel.

11. A surgical aspirator device comprising:
   (a) an elongated sleeve comprising a distal end and a proximal end, a female coupling member formed at the proximal end, and a plurality of apertures formed in the sleeve at a location spaced from the female coupling member;
   (b) an elongated substantially rigid aspirator tip comprising a hollow tubular neck member, said neck member defining at least one opening in a distal end of the neck member to allow fluid and material to enter the neck member;
   (c) a male coupling member located at a proximal end of the hollow neck member and defining an internal channel in communication with an interior of the hollow neck member allowing gases, fluid, or materials to flow between the interior of the hollow neck member and the internal channel of the male coupling member, wherein the male coupling member has a thickness extending between an exterior portion of the male coupling member and the internal channel of the male coupling member, wherein the male coupling member comprises at least one groove extending longitudinally along at least a portion of the exterior portion of the male coupling member, the at least one groove being of a depth less than the thickness of the male coupling member;
   (d) wherein the elongated sleeve is couplable to the elongated aspirator tip by inserting the male coupling member into the female coupling member to form a frictionally engaged coupled region; and
   (e) at least one venting channel in communication with an interior of the sleeve and the external environment is formed between the at least one groove of the male coupling member and an internal surface of the female coupling member, allowing airflow between the external environment and the interior of the sleeve.

12. The surgical aspirator device of claim 11, wherein:
   (a) said elongated aspirator tip further comprising a handle member manually graspable during use and having portions defining a longitudinal internal channel, said handle member comprising:
      (i) said at least one groove extending longitudinally along at least a portion of the exterior portion of the male coupling member further extending longitudinally along said handle member;
      (ii) said male coupling member located at a distal end of the handle member;
      (iii) a vacuum tube coupling member located at a proximal end of the handle member; and
      (iv) said hollow tubular neck member attached to the male coupling member of the handle member so that an interior of the hollow tubular neck member is in communication with the longitudinal internal channel of the handle member; and
   (b) when the elongated sleeve is coupled to the elongated aspirator tip, the internal surface of the female coupling member is not in continuous contact with the male coupling member along the at least one groove of the male coupling member, thereby forming at least one venting channel therebetween for allowing air to flow between the exterior environment and the interior of the sleeve.

13. The surgical aspirator device of claim 11, wherein the surgical aspirator tip further comprises an elongated manually graspable grip member extending from a proximal end of the male coupling member and exterior of the elongated sleeve when the male coupling member is inserted within the female coupling member.

14. The surgical aspirator device of claim 13, wherein the elongated manually graspable grip member comprises at least one longitudinal exterior groove that is in communication with the at least one groove of the male coupling member.

15. The surgical aspirator device of claim 11, wherein an elongated grip member is attached to a proximal end of the male coupling member, the elongated grip member defining an internal channel that is in communication with the internal channel in the male coupling member allowing gases, fluid, or materials to flow between the internal channel in the male coupling member and the internal channel of the elongated grip member.

16. The surgical aspirator device of claim 11, wherein at least one portion of the female coupling member defining a portion of the at least one venting channel comprises at least one cross-hole in communication with an interior of the venting channel and the external environment.

17. The surgical aspirator device of claim 11, wherein a tip guard is located at a distal end of the hollow tubular neck member, the tip guard including a plurality of openings in communication with the at least one opening in the distal end of the hollow tubular neck member.

18. The surgical aspirator device of claim 13, wherein a distal end of the elongated grip member is positioned to abut a proximal end of the female coupling member when the male coupling member is inserted into the female coupling member to substantially prevent longitudinal movement of the sleeve along the elongated aspirator tip in a first direction.

19. The surgical aspirator device of claim 15, wherein the elongated grip member has a thickness extending between an exterior portion of the grip member and the internal channel of the grip member, and wherein the elongated grip member includes at least one longitudinal exterior groove extending along the exterior of the grip member that is in communication with the at least one groove of the male coupling member, the at least one longitudinal groove extending along the exterior portion of the grip member being of a depth less than the thickness of the grip member.

20. An elongated surgical aspirator tip, comprising:
   (a) a substantially rigid neck having an internal channel and at least one opening in a distal end of the neck to allow fluid and material to enter the neck;
   (b) a male coupling member extending from a proximal end of the neck, the male coupling member defining an internal channel that is in communication with the internal channel of the neck, the male coupling member having a thickness extending between an exterior surface of the male coupling member and the internal channel of the male coupling member; and
   (c) at least one longitudinal groove extending along at least a portion of the male coupling member, wherein the at least one longitudinal groove does not extend onto the neck, the at least one longitudinal groove defined by at least one surface extending inwardly from the exterior surface of the male coupling member to define a groove cross-sectional shape, the at least one longitudinal groove being of a depth less than the thickness of the male coupling member.

21. The surgical aspirator tip of claim 20, further comprising an elongated grip member located at a proximal end of the male coupling member, said grip member shaped and sized to be manually graspable.

22. The surgical aspirator tip of claim 21, wherein the elongated grip member comprises at least one longitudinal groove extending along the elongated grip member, said at least one longitudinal groove of the elongated grip member in communication with the at least one longitudinal groove of the male coupling member.

23. The surgical aspirator tip of claim 22, wherein the elongated grip member defines an internal channel that is in communication with the internal channel in the male coupling member, and further wherein the elongated grip member has a thickness extending between an exterior surface of the elongated grip member and the internal channel of the grip member, and wherein the at least one longitudinal groove extending along the exterior of the grip member is of a depth less than the thickness of the grip member.

24. The surgical aspirator tip of claim 20, wherein a tip guard is located at the distal end of the neck, the tip guard including a plurality of openings in communication with the at least one opening in the distal end of the neck.

25. The surgical aspirator tip of claim 20, wherein the neck is a metal cannula and the male coupling member is molded onto a proximal end portion of the neck.

* * * * *

UNITED STATES PATENT AND TRADEMARK OFFICE
CERTIFICATE OF CORRECTION

| | |
|---|---|
| PATENT NO. | : 7,794,421 B2 |
| APPLICATION NO. | : 11/303702 |
| DATED | : September 14, 2010 |
| INVENTOR(S) | : R. J. Yarger |

It is certified that error appears in the above-identified patent and that said Letters Patent is hereby corrected as shown below:

| COLUMN | LINE | ERROR |
|---|---|---|
| (75) | Inventor | "Richard J Yarger," should read |
| Pg. 1, col. 1 | | --Richard J. Yarger,-- |

Signed and Sealed this
Fourteenth Day of June, 2011

David J. Kappos
*Director of the United States Patent and Trademark Office*